(12) United States Patent
Jang (10) Patent No.: US 6,824,554 B1
(45) Date of Patent: Nov. 30, 2004

(54) CONVERTIBLE MODE VASCULAR CATHETER SYSTEM

(75) Inventor: G. David Jang, Redlands, CA (US)

(73) Assignee: Advanced Cardiovascular Systems, Inc., Santal Clara, CA (US)

(*) Notice: Subject to any disclaimer, the term of this patent is extended or adjusted under 35 U.S.C. 154(b) by 1826 days.

(21) Appl. No.: 07/714,642

(22) Filed: Jun. 13, 1991

Related U.S. Application Data (63) Continuation-in-part of application No. 07/705,295, filed on May 24, 1991.

(51) Int. Cl.$^7$ .............................................. A61M 29/00
(52) U.S. Cl. ...................................... 606/194; 604/160
(58) Field of Search .............................. 604/52, 53, 95, 604/96, 160, 161, 165, 263, 280–284; 128/656–658, 772; 606/194

(56) References Cited

U.S. PATENT DOCUMENTS

| | | | |
|---|---|---|---|
| 3,262,449 A | | 7/1966 | Pannier et al. |
| 3,297,030 A | | 1/1967 | Czorny et al. |
| 3,550,591 A | | 12/1970 | MacGregor |
| 3,682,173 A | | 8/1972 | Center |
| 3,853,130 A | | 12/1974 | Sheridan |
| 4,037,599 A | | 7/1977 | Raulerson |
| 4,054,136 A | * | 10/1977 | von Zeppelin ............... 604/160 |
| 4,079,738 A | * | 3/1978 | Dunn et al. .................. 604/165 |
| 4,147,165 A | | 4/1979 | Tauschinski |
| 4,175,564 A | | 11/1979 | Kwak |
| 4,323,071 A | | 4/1982 | Simpson et al. |
| 4,411,055 A | | 10/1983 | Simpson et al. |
| 4,411,654 A | | 10/1983 | Boarini et al. |
| 4,439,185 A | | 3/1984 | Lundquist |
| 4,468,224 A | | 8/1984 | Enzmann et al. |
| RE31,855 E | | 3/1985 | Osborne |
| 4,516,972 A | | 5/1985 | Samson |

(List continued on next page.)

FOREIGN PATENT DOCUMENTS

| | | |
|---|---|---|
| EP | 0274129 A2 | 7/1988 |
| EP | 0282143 A1 | 9/1988 |
| EP | 0388112 A2 | 9/1990 |
| EP | 0416662 B1 | 3/1991 |
| WO | WO 82/03558 | 10/1982 |
| WO | WO 91/05512 | 5/1991 |
| WO | WO 92/17236 | 10/1992 |

OTHER PUBLICATIONS

Suggested Directions for Use, Outsider™ Ultra Low Profile Coronary Balloon Dilatation Catheter, Mansfield, Boston Scientific Corporation.

Primary Examiner—Cary E. O'Connor
(74) Attorney, Agent, or Firm—McAndrews, Held & Malloy, Ltd.

(57) ABSTRACT

An angioplasty catheter comprising a catheter shaft having a proximal portion and a distal end, an angioplasty balloon attached to the shaft at the distal end, a balloon inflation lumen extending through the shaft and communicating with the interior of the balloon, a guidewire lumen extending through the shaft and through the balloon for receiving a steerable guidewire, the guidewire lumen having an outside wall, wherein the guidewire lumen has a proximal opening located at a point normally outside of the patient during use of the catheter for insertion of a guidewire into the lumen, and a side port adapted to permit passage of a guidewire into the lumen through the outside wall of the guidewire lumen, the side port located distally of the proximal opening and at a point normally inside of the patient during use, and guidewire removing means in the outside wall of the guidewire lumen extending from the proximal opening to the side port for permitting a guidewire in the guidewire lumen to be moved laterally from the guidewire lumen though the outside wall of the guidewire lumen. Also disclosed are a removable "Y" connector and methods for using the catheter and for exchanging catheters and guidewires during vascular catheterization procedures.

4 Claims, 10 Drawing Sheets

U.S. PATENT DOCUMENTS

| | | | |
|---|---|---|---|
| 4,538,622 A | | 9/1985 | Samson et al. |
| 4,554,929 A | | 11/1985 | Samson et al. |
| 4,569,347 A | | 2/1986 | Frisbie |
| 4,573,470 A | | 3/1986 | Samson et al. |
| 4,581,017 A | | 4/1986 | Sahota |
| 4,582,181 A | | 4/1986 | Samson |
| 4,585,013 A | | 4/1986 | Harris |
| 4,596,559 A | | 6/1986 | Fleischhacker |
| 4,616,652 A | | 10/1986 | Simpson |
| 4,619,644 A | | 10/1986 | Scott |
| 4,631,056 A | | 12/1986 | Dye |
| 4,638,805 A | | 1/1987 | Powell |
| 4,705,507 A | | 11/1987 | Boyles |
| 4,738,666 A | | 4/1988 | Fuqua |
| 4,747,833 A | * | 5/1988 | Kousai et al. .............. 604/161 |
| 4,748,982 A | | 6/1988 | Horzewski et al. |
| 4,748,986 A | | 6/1988 | Morrison et al. |
| 4,762,129 A | | 8/1988 | Bonzel |
| 4,771,777 A | | 9/1988 | Horzewski et al. |
| 4,821,722 A | | 4/1989 | Miller et al. |
| 4,865,593 A | | 9/1989 | Ogawa et al. |
| 4,883,468 A | | 11/1989 | Kousai et al. |
| 4,888,000 A | * | 12/1989 | McQuilkin et al. ......... 604/160 |
| 4,898,577 A | | 2/1990 | Badger et al. |
| 4,931,049 A | * | 6/1990 | Klimas ....................... 604/165 |
| 4,944,745 A | | 7/1990 | Sogard |
| 4,947,864 A | * | 8/1990 | Shockey et al. ............ 128/772 |
| 4,981,478 A | | 1/1991 | Evard et al. |
| 4,988,356 A | | 1/1991 | Crittenden et al. |
| 4,997,424 A | * | 3/1991 | Little ........................ 604/161 |
| 5,024,234 A | | 6/1991 | Leary et al. |
| 5,034,001 A | | 7/1991 | Garrison et al. |
| 5,046,503 A | | 9/1991 | Schneiderman |
| 5,061,267 A | | 10/1991 | Zeiher |
| 5,061,273 A | | 10/1991 | Yock |
| 5,102,403 A | * | 4/1992 | Alt ............................. 128/772 |
| 5,135,482 A | | 8/1992 | Neracher |
| 5,135,535 A | | 8/1992 | Kramer |
| 5,154,725 A | | 10/1992 | Leopold |
| 5,171,222 A | | 12/1992 | Euteneuer et al. |
| 5,195,978 A | | 3/1993 | Schiffer |
| 5,205,822 A | | 4/1993 | Johnson et al. |
| 5,267,982 A | | 12/1993 | Sylvanowicz |
| 6,273,899 B1 | | 8/2001 | Kramer |
| 6,398,799 B2 | | 6/2002 | Kramer |

* cited by examiner

CONVERTIBLE MODE VASCULAR CATHETER SYSTEM

CROSS REFERENCE TO RELATED APPLICATIONS

This application is a continuation in part of copending U.S. application Ser. No. 07/705,295, filed May 24, 1991.

This invention relates to vascular catheters (such as angioplasty catheters) specially adapted for rapid exchange of both the guidewire and the catheter during use. It also relates to the method of using those catheters.

Percutaneous transluminal coronary angioplasty (PTCA) has emerged as the major viable present alternative to bypass surgery for revascularization of stenotic and occluded coronary arteries. Although transluminal angioplasty has application in peripheral artery disease, it is most widely used in the treatment of coronary artery disease. Unlike bypass surgery, percutaneous angioplasty does not require general anesthesia, cutting of the chest wall, extracorporeal perfusion, or transfusion of blood. Percutaneous coronary angioplasty is not only less invasive and less traumatic to the patient, it is also less expensive because the angioplasty patient will have a shorter hospital stay and shorter post-procedure recovery time.

Percutaneous transluminal angioplasty is performed by making a skin puncture with a specially-designed needle in one of the groins, and then introducing a guiding catheter (typically 8 or 9 French size) into the aorta and coronary artery orifice. A smaller caliber catheter which has a built-in inflatable and deflatable balloon of predetermined size and diameter is passed through the guiding catheter which is positioned in the opening of a target artery. This balloon catheter (with the balloon totally deflated by negative pressure) is advanced inside the target artery toward the point of obstruction that needs to be dilated. The guidewire plays an essential role in leading the balloon catheter to the target coronary artery in safety and non-traumatic fashion. With the balloon portion of the catheter properly positioned inside the obstructed segment of the artery, under X-ray fluoroscopic observation, the balloon is inflated by injecting contrast media mixed with saline at a pressure sufficient to overcome the resistance of the arteriosclerotic plaque of the obstructed segment.

By inflating the balloon in the stenosis multiple times over a period of between 10–30 seconds and one or two minutes (allowing blood flow between inflations), the desired dilation of the obstructed segment of the artery can be achieved. When the desired results have been obtained by balloon inflations, the guiding catheter, the balloon catheter (with the balloon completely deflated with negative pressure) and the guidewire are withdrawn from the artery and the patient, and the procedure is successfully terminated.

The size and diameter of the balloon to be used in a transluminal angioplasty should be approximately matched to the size and native diameter of the obstructed segment of the artery to be dilated. If the balloon size and diameter is smaller than the native artery, the results of balloon angioplasty are suboptimal, requiring a second dilation with a larger-sized balloon, and if balloon size is too large for the native artery, complications may occur due to arterial wall damage.

During the angioplasty procedure, a guidewire is first advanced into the desired location, after which the angioplasty catheter is advanced over the guidewire. It is sometimes necessary to replace (or exchange) either the guidewire or the balloon catheter during the procedure.

If the balloon is undersized, for example, the catheter must be withdrawn and replaced with a larger balloon catheter in order to permit adequate dilatation of the lesion. With conventional over-the-wire catheters, in which the guidewire lumen extends the entire length of the catheter shaft, a guidewire extension (e.g., 145 cm long) must first be attached to the regular guidewire (e.g., 175 cm long) being used outside the patient before the catheter is withdrawn. This permits the distal end of guidewire to be held in position while the catheter is removed and a new catheter is exchanged. Usually, two to three operators are needed to effect such a catheter exchange.

The catheter disclosed in U.S. Pat. No. 4,762,129 avoids the necessity for extending the guidewire or exchange guidewire (e.g., 300 cm in length) by having a short guidewire lumen that extends substantially only through the distal end of the catheter. This type of catheter is referred to herein as a rapid-exchange catheter. Thus, the guidewire is outside the catheter shaft for much of the catheter length, and is inside the catheter at only the distal end. The catheter can be exchanged without extending the 175 cm regular guidewire, and the exchange can be effected by one or two operators. However, this catheter has a serious drawback of not being able to permit ready exchange of guidewires. In clinical practice, the need for guidewire exchange is more common.

Conventional over-the-wire angioplasty catheters, with a guidewire lumen extending their entire length, permit simple guidewire exchange. During angioplasty procedures, the guidewire tip may become damaged, may be needed of a different type of guidewire or may need to be reshaped to complement the patient's vasculature. The guidewire exchange procedure is readily accomplished with such a conventional over-the-wire catheter. However, with the rapid-exchange type catheter of U.S. Pat. No. 4,762,129, guidewire exchange requires complete removal and reinsertion of both the guidewire and the angioplasty catheter; thus, defeating the original goal of expedient advantage of the rapid-exchange catheter.

Another disadvantage of the rapid-exchange catheter is back bleeding. While the guidewire is being manipulated to select the target vessel or to cross the culprit lesion, the Tuehy-Borst adapter must be loosened. This, in turn, permits backbleeding to occur.

Accordingly, there is a need for an angioplasty catheter that permits rapid-exchange of both the catheter and the guidewire. There is also a need for a catheter that will permit the user to select the mode of usage between the rapid-exchange and the over-the-wire systems.

SUMMARY OF THE INVENTION

In accordance with one aspect of the present invention, there is provided an angioplasty catheter comprising a catheter shaft having a proximal portion and a distal end, an angioplasty balloon attached to the shaft at the distal end, a balloon inflation lumen extending through the shaft and communicating with the interior of the balloon, a guidewire lumen extending through the shaft and through the balloon for receiving a steerable guidewire, the guidewire lumen having an outside wall, wherein the guidewire lumen has a proximal opening located at a point normally outside of the patient during use of the catheter for insertion of a guidewire into the lumen, and a side port adapted to permit passage of a guidewire into the lumen through the outside wall of the guidewire lumen, the side port located distally of the proximal opening and at a point normally inside of the patient during use, and guidewire removing means in the outside wall of the guidewire lumen extending from the proximal opening to the side port for permitting a guidewire in the guidewire lumen to be moved laterally from the guidewire lumen though the outside wall of the guidewire lumen. In one embodiment, the side port is located adjacent to and proximally of the balloon, preferably within about 35 cm of the balloon. One embodiment of the guidewire removing means is a slit through the outside wall of the catheter shaft. This slit may be continuous from the proximal opening to the side port, or may be discontinuous, forming a perforated line from the proximal opening to the side port. In another embodiment, the guidewire removing means is a weakened area of the wall of the guidewire lumen adapted to be severed for removal of the guidewire therethrough. One variation of the invention provides a second side port communicating with the interior of the guidewire lumen. Another provides a perfusion opening communicating with the interior of the guidewire lumen, the perfusion opening located between the side port and the balloon. Still another embodiment includes a "Y" connector at the proximal opening having an axial portion through which the balloon inflation lumen extends and a side portion through which the guidewire may be inserted into the guidewire lumen, wherein at least a portion of the connector can be removed from the catheter shaft to permit a guidewire extending through the connector and into the guidewire lumen to be removed through the guidewire removing means. The connector is advantageously adapted to be separated longitudinally and at least a portion thereof removed from the catheter shaft. In one variation, the connector comprises two longitudinally separable portions having first and second longitudinal sides on different sides of the catheter shaft, the portions being hingedly joined at the first longitudinal side and separably joined at the second longitudinal side.

Another embodiment of the present invention comprises an intravascular catheter comprising a catheter shaft having a proximal end and a distal end, wherein a portion of the catheter including the distal end is normally inside a patient during use and the proximal end is normally outside the patient or outside the guiding catheter, a guidewire lumen extending through the shaft for receiving a steerable guidewire, wherein the guidewire lumen has an outside wall, and a proximal opening at the proximal end of the shaft for insertion of a guidewire into the lumen, and means formed in the outside wall of the guidewire lumen extending distally from the proximal opening to a point normally inside the patient during use of the catheter for permitting a guidewire in the guidewire lumen to be moved laterally from the guidewire lumen though the outside wall of the guidewire lumen. The guidewire removing means may be a slit, fully formed or inchoate. The catheter preferably includes a side port through the outside wall of the guidewire lumen for passage of a guidewire into the lumen through the side of the catheter shaft, the side port located distally of the proximal opening and normally inside of a patient during use of the catheter. In one embodiment of the catheter, the guidewire removing means is a slit and the slit is continuous from the proximal opening to the side port. In another, the guidewire removing means is a slit and the slit is discontinuous, forming a perforated line from the proximal opening to the side port. In still another embodiment, the guidewire removing means is a weakened area of the wall of the guidewire lumen adapted to be severed for removal of the guidewire therethrough. According to one modification, the catheter may further comprise a second side port communicating with the interior of the guidewire lumen.

The present invention also includes a catheter for use in an animal body with a guidewire, comprising a catheter shaft having a proximal end and a distal end with at least two lumens extending therethrough, and a "Y" connector surrounding at least a portion of the proximal end of the catheter shaft and having at least two arms, one arm providing an access channel into one of the lumens and another arm providing an access channel into another of the lumens, wherein the "Y" connector has at least two segments joined together in a separable manner along a longitudinal line so that upon separation of the segments, the "Y" connector no longer surrounds the portion of the proximal end of the catheter shaft. In one embodiment, upon separation of the segments, one of the segments is completely removable from the catheter shaft. In another embodiment, upon separation of the segments, the connector is completely removable from the catheter shaft in such a manner that an elongate object extending through one arm of the connector into a lumen of the catheter shaft can remain in the lumen during such removal of the connector.

The invention further includes a method of removing a catheter during a procedure involving vascular catheterization, comprising the steps of providing a catheter of the type described above having a guidewire passing through the guidewire lumen from the proximal opening to the distal opening thereof and positioning the catheter in a patient with the proximal end of the guidewire extending out of the proximal opening, holding the proximal end of the guidewire to maintain the positioning of the guidewire in the patient while removing the catheter from the patient by moving the guidewire laterally out of the guidewire lumen through the guidewire removing means until the entire catheter is outside the patient and outside the guiding catheter and a portion of the guidewire is exposed at the distal end of the catheter, and then holding the exposed portion of the guidewire and removing the catheter off of the proximal end of the guidewire. The method may also include inserting another catheter, with the guidewire in the guidewire lumen at the distal portion of the catheter and either remaining in the guidewire lumen for the entire length of the catheter that is inside the patient during use, or extending out through the side of the catheter and running parallel to the catheter proximal of the distal portion of the catheter.

DETAILED DESCRIPTION OF THE INVENTION

Figure 1:
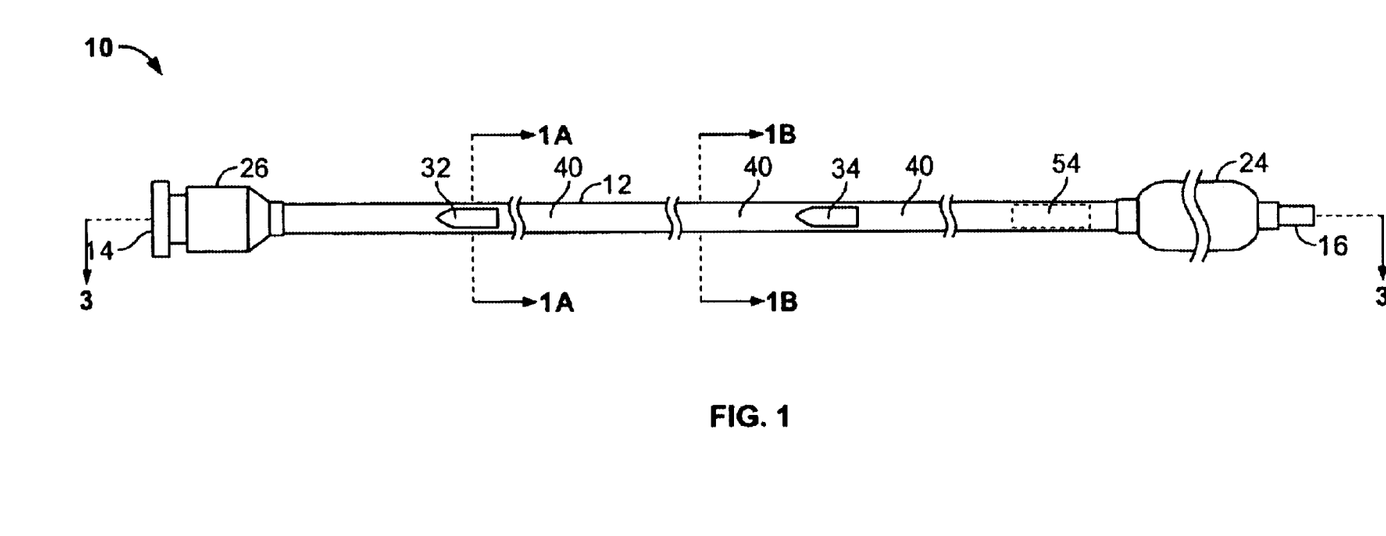
FIG. 1 is a foreshortened plan view of a catheter according to the present invention.
Figure 1A:
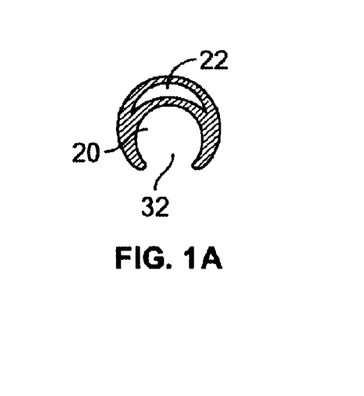
FIG. 1A is a transverse cross section of the catheter of FIG. 1, taken along the line A—A.

A basic embodiment of the catheter of the present invention is illustrated in FIG. 1. A catheter 10 is provided with a catheter shaft 12 extending from a proximal end 14 to a distal end 16. As shown more clearly in FIG. 1B, the interior of the catheter shaft 12 has a guidewire lumen 20 and a balloon inflation lumen 22 extending through the catheter shaft 12.

The catheter 10 has an angioplasty balloon 24 at the distal end 16 thereof. At the proximal end 14 of the catheter shaft 12, a balloon inflation connector 26 is provided in fluid communication with the balloon lumen 22. Fluid introduced into the proximal end of the balloon inflation connector 26 can travel through the balloon lumen 22 and into the interior of the balloon 24 to inflate and deflate the balloon 24 during an angioplasty procedure. The balloon inflation lumen 22 terminates inside the balloon 24. The opposite end of the balloon inflation lumen 22 terminates inside the balloon inflation connector 26.

Figures 1B, 1C:
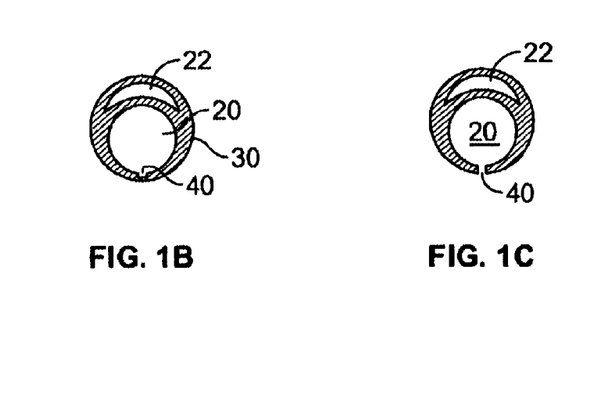
FIG. 1B is a transverse cross section of the catheter of FIG. 1, taken along the line B—B.
FIG. 1C is a transverse cross section of the catheter of FIG. 1 corresponding to FIG. 1B, but illustrating the opening of the guidewire removing means.

The guidewire lumen 20 is adapted to receive a steerable guidewire and has an outside wall 30 (shown in FIG. 1B).

A proximal opening 32 is provided through the outside wall 30 of the guidewire lumen 20. This proximal opening 32 is situated in the proximal portion of the catheter shaft 12 at a location sufficiently close to the proximal end 14 that it is normally outside of the patient during the angioplasty (or other vascular procedure). Typically, the proximal opening 32 will be within 60 cm, preferably within about 40 cm, more preferable within about 30 cm of the proximal end 14 of the catheter 10.

The balloon 24 is made in accordance with conventional techniques for fabricating angioplasty balloons. Preferably, it is either blown from the distal end 16 of the catheter shaft 12, or is blown or formed of a separate piece of material which is bonded to the distal end of 16 of the catheter shaft 12. The balloon 24 may advantageously be formed of relative inelastic polymer material, such as polyethylene, polypropylene, polyvinylchloride, polyethylene terephthalate, and the like.

The catheter shaft 12 is also provided with a side port 34 which extends through the outside wall 30 of the guidewire lumen 20. The side port 34 is located distally of the proximal opening 32, and is located at a point normally inside of the patient when the catheter is properly placed for performance of an angioplasty procedure. Preferably, the side port 34 is located proximally of the balloon 24 and within 80 cm, preferably 60 cm, and more preferably about 40 cm of the balloon 24.

The catheter 10 of the present invention is provided with a means for removing a guidewire that is inside of the guidewire lumen out of the guidewire lumen 20 through the outside wall 30 of the guidewire lumen 20. If the catheter shaft 12 or the guidewire is considered to extend in a longitudinal or axial direction, this movement of the guidewire out of the guidewire lumen 20 can be considered as a sideways, radial, or transverse motion of the guidewire. The guidewire removing means 40 is adapted to form a slit through the outside wall 30 of the guidewire lumen 20 through which the guidewire may be removed from inside the guidewire lumen 20. The guidewire removing means 40 may be an actual slit cut entirely through the side wall 30 of the guidewire lumen 20 as illustrated in FIG. 1C. Alternatively, it may be an inchoate slit such as the weakened area illustrated in FIG. 1B. The guidewire removing means 40 may be cut entirely through the outside wall 30 of the guidewire lumen 20 only in certain sections, leaving other section at least partially intact, to form a sort of perforated line. It may be formed of a different material than the remainder of the catheter shaft 12 and even of a different material than the adjacent portions of the outside wall 30 of the guidewire lumen 20.

One advantage of having only an inchoate slit is that it prevents backbleeding out of the guidewire removing means 40 during performance of the procedure. It is possible, however, to use an inchoate slit for only the portion of the guidewire removing means 40 that is outside of the guiding catheter in use. The remainder of the guidewire removing means 40 that is outside the patient and outside the guiding catheter can be a fully formed slit or a perforated slit without creating backbleeding problems.

Figure 2:
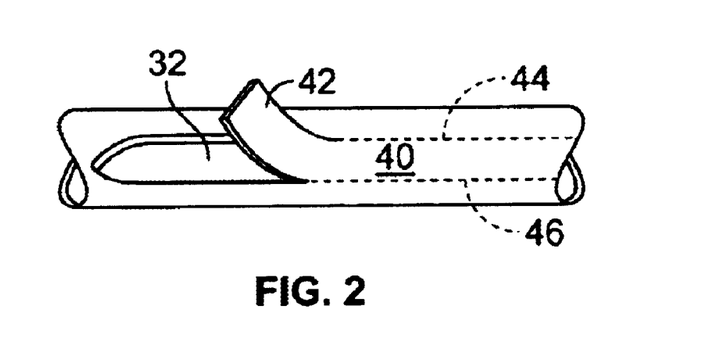
FIG. 2 is a fragmentary view of a portion of the catheter shaft of the FIG. 1 catheter surrounding the proximal opening, illustrating one variation of the guidewire removing means.

As illustrated in FIG. 2, the guidewire removing means 40 may comprise a removable tear strip 42 defined by a pair of weakened lines 44, 46 extending distally from the proximal opening 32.

The guidewire removing means 40 extends from the proximal opening 32 distally along the length of the catheter shaft 12 to a point that is ordinarily inside the patient when the catheter 10 is properly placed for performance of an angioplasty procedure. Thus, the guidewire removing means 40 begins at a point ordinarily outside the patient and outside the guiding catheter upon proper placement of the catheter 10 and extends distally to a point ordinarily inside the patient upon such placement. From another perspective, it can be said that the guidewire removing means 40 extends distally for at least 40 cm, preferably at least 60 or 70 cm, and more preferably at least 80, 90 or 100 cm.

The guidewire removing means 40 may advantageously extend distally to the side port 34, and in one embodiment of the invention, may extend an additional distance distally beyond the side port 34. The guidewire removing means 40 preferably terminates proximally of the balloon 24, and may be immediately adjacent the balloon 24 or may be 5 cm, 10 cm, or more proximally of the balloon 24.

If the guidewire removing means 40 is not a slit prior to its use, it becomes a slit or opening after use, as illustrated in FIG. 1C.

Figure 3:
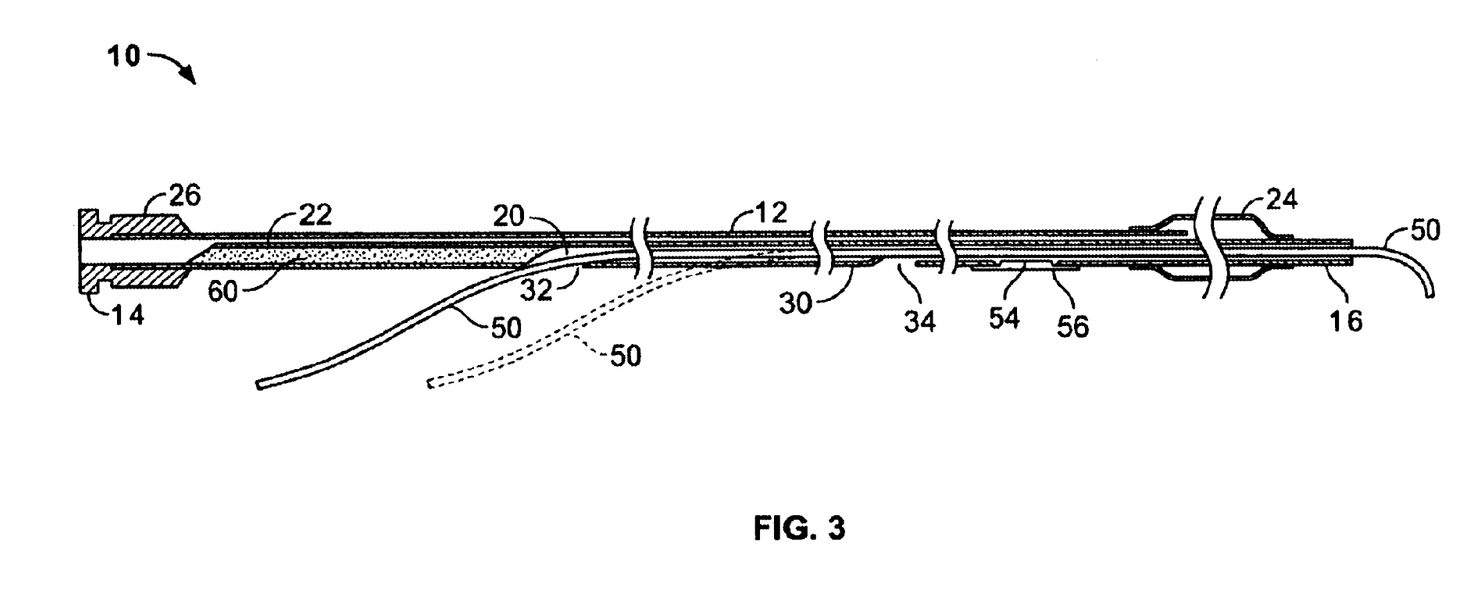
FIG. 3 is a longitudinal cross section of the catheter of FIG. 1 taken along the line 3—3, illustrating the guidewire in place and the function of the guidewire removing means.

The use of the catheter 10 of the present invention is illustrated in FIG. 3. In this longitudinal cross sectional view, the catheter 10 is illustrated with a guidewire 50 in place in the guidewire lumen 20. The proximal portion of the guidewire 50 is outside of the catheter 10. The guidewire 50 passes through the proximal opening 32 into the guidewire lumen 20, and is inside the guidewire lumen 20 for the entire length of the catheter shaft 12 that extends distally from the proximal opening 32. The distal end of the guidewire 50 extends out of the distal end 16 of the catheter shaft 12.

Figure 4:
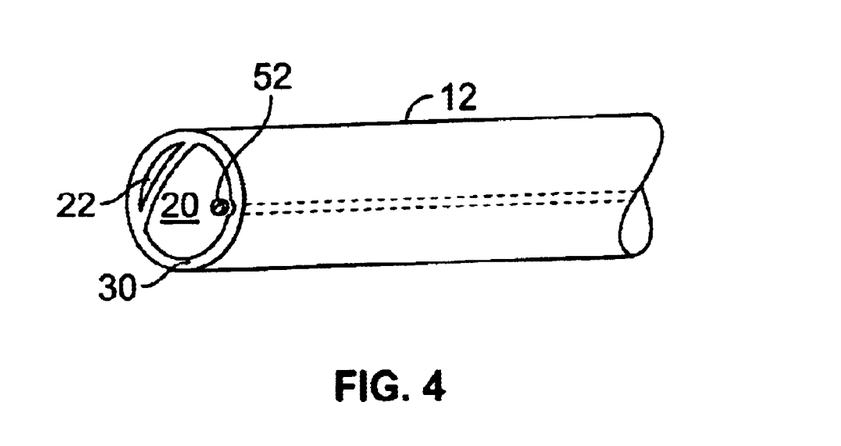
FIG. 4 is a cross sectional fragmentary perspective view of the catheter of FIG. 1, taken along the line B—B, illustrating another variation of the guidewire removing means.

When the guide wire is to be removed radially or laterally out of the guidewire lumen 20, the guidewire removing means 40 provides a slit or opening in the outside wall 30 of the guidewire lumen 20 through which the guidewire 50 may be removed from the guidewire lumen 20. This slit or opening, if not fully formed, may be completed by cutting the outside wall 30 of the guidewire lumen 20, by tearing or rupturing a weakened area in the outside wall 30, or by tearing loose a removable strip (as illustrated in FIG. 2). In a preferred embodiment the guidewire removing means 40 is a weakened area that is fully opened only when the guidewire 50 is removed through the guidewire removing means 40. In one embodiment, the guidewire 50 is simply pulled through the outside wall 30 of the guidewire lumen 20. Alternatively, as illustrated in FIG. 4, the catheter shaft 12 may be provided with a filament 52 in association with the guidewire removing means 40. The filament 52 may be a continuous fiber or strand extending along the length of the guidewire removing means and inside at least a portion of the outside wall 30 of the guide wire lumen 20. When the filament 52 is pulled outwardly, it tears a slit into the outside wall 30 of the guidewire lumen 20.

In FIG. 3, the initial removal of the guidewire 50 through the guidewire removing means 40 is illustrated in phantom. In that figure, a phantom guidewire 50 is illustrated extending through the outside wall 30 of the guidewire lumen 20 at a point distally of the proximal opening 32.

Figure 5:
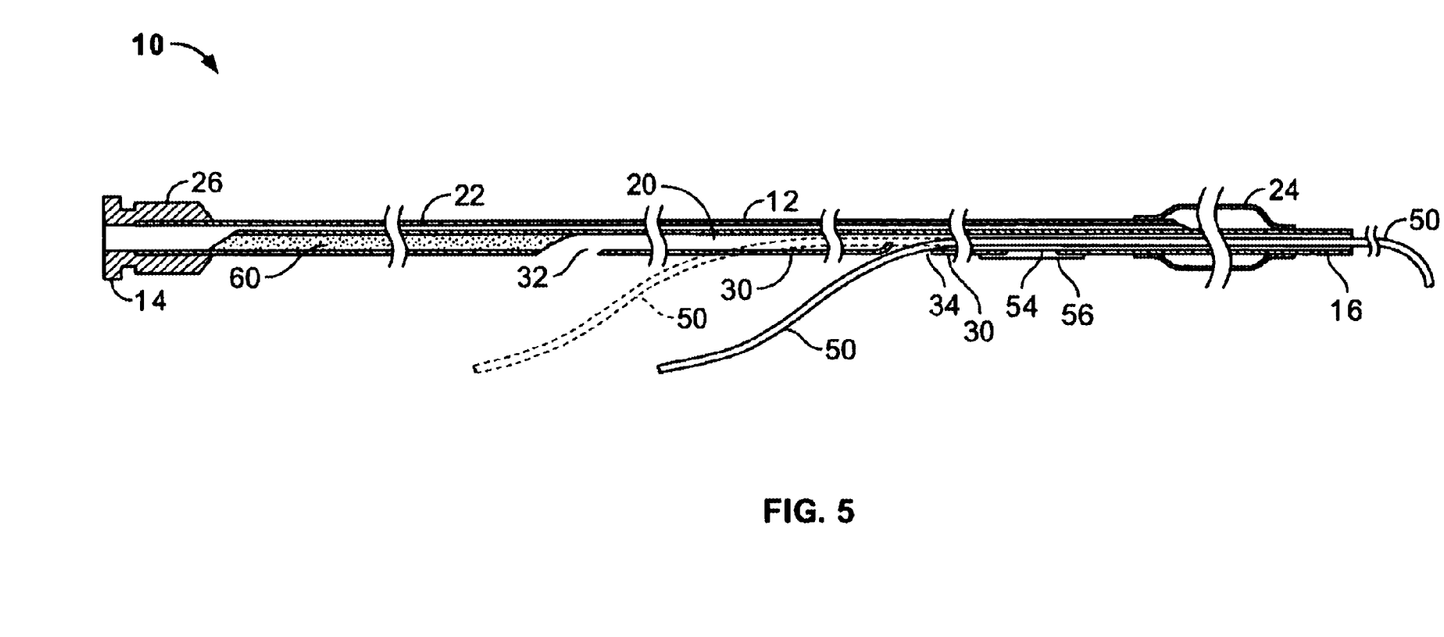
FIG. 5 is a longitudinal cross section corresponding to FIG. 3, illustrating movement of the guidewire laterally out of the guidewire removing means.

As illustrated in FIG. 5, the phantom guidewire 50 is pulled through the outside wall 30 of the guidewire lumen 20 until the guidewire 50 has been removed through the outside wall 30 up to the side port 32. It will be understood, of course, that in accordance with the present invention, the guidewire 50 may be removed through the outside wall 30 to a point proximal of or distal of the side port 34; however, in a preferred embodiment, the lateral removal out of the guidewire lumen 20 continues up to the side port 34.

It should be noted that the removal of the proximal portion of the guidewire 50 through the outside wall 30 can be accomplished without longitudinal or axial movement of the distal portion of the guidewire 50. Thus, in FIG. 3, the distal tip of the guidewire 50 is in the same position as in FIG. 5; however, in FIG. 5, the guidewire has been removed laterally through the guidewire removing means along a portion of the length of the catheter shaft 12.

In the simplest embodiment of the present invention the guidewire lumen 20 may be provided simply with a proximal opening 32, a side port 34, and guidewire removing means 40 extending distally of the proximal opening 32 at least to the side port 34, and perhaps beyond.

However, more sophisticated versions of the present invention are also contemplated. In one such embodiment, a distal side opening 54 may be provided through the outside wall 30 of the guidewire lumen 20 to provide access into the guidewire lumen 20 at a point distal of the sideport 34. The distal side opening 54 may be open in normal use; however, the distal side opening 54 is preferably covered with a removable patch 56, as best seen in FIGS. 3 and 5. The removable patch 56 is preferably made of foil, Mylar, aluminized or metalized Mylar, or other suitable material, and may be held in place with an adhesive. The removable patch 56 may be removed from the catheter shaft 12 to open up the distal side opening 54 to permit extension of the guidewire 50 through the distal side opening 54 or to permit use of the distal side opening 54 as a perfusion opening. In one embodiment of the invention, the guidewire, removing means 40 extends distally to the distal side of the distal side opening 54.

The portion of the guidewire lumen 20 located proximally of the proximal opening 32 is preferably closed, and may be filled with a filler 60 such as a polymer material formed in place or a stylet inserted in a waterproof manner into the guidewire lumen 20, as illustrated in FIGS. 3 and 5.

Figure 6:
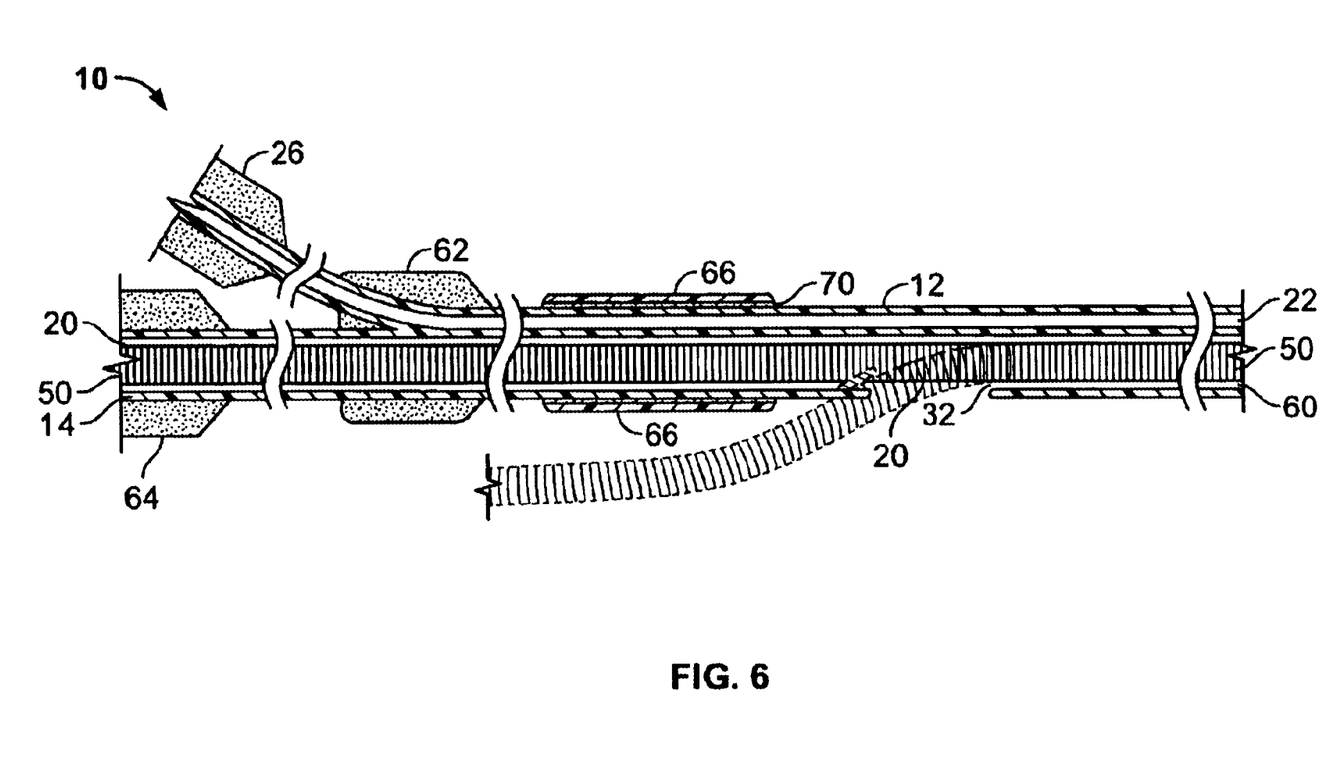
FIG. 6 is a foreshortened longitudinal cross section of the proximal end of one embodiment of the catheter of the present invention.

In an alternative embodiment of, the invention, the catheter of FIG. 1 is modified at its proximal end as illustrated in FIG. 6. Specifically, this particular catheter has a conventional "Y" connector 62 at the proximal end 14 of the catheter shaft 21 has the balloon inflation connector 26 and a guidewire connector 64 at the two "branches" of the "Y". The guidewire lumen 20 extends from the proximal end 14 of the catheter shaft 10 through the guidewire connector 64 and the "Y" connector 62 and extends distally the length of the catheter shaft 12.

The proximal opening 32 is located distally of the "Y" connector 62. The catheter 10 is provided with a sliding cover 66 that is axially movable to cover or uncover the proximal opening 32. The sliding cover 66 is preferably an annular sleeve circling the catheter shaft 12 and axially movable with respect thereto. The sliding cover 66 preferably has a soft sealing material 70 (such as a pliable closed cell polymer foam, a silicone elastomer, or other suitable material) on its inside surface to provide a seal against the catheter shaft 12. Ordinarily, the sliding cover 66 is over the proximal opening 32, closing and sealing the proximal opening 32.

In an alternative embodiment, the sliding cover 66 may be replaced by a removable covering (not illustrated) similar to the removable patch 56 to close the proximal opening 32 until it is used.

In ordinary use, the guidewire 50 extends distally through the guidewire connector 64, the remainder of the "Y" connector 62, inside the guidewire lumen 20, past the proximal opening 32, and out of the distal end 16 of the catheter 10. When required (as will be explained in more detail hereafter), the sliding cover 66 or other seal covering the proximal opening 32 is removed, the catheter 10 is maintained in place in the patient while the guidewire 50 is removed proximally out of the guidewire connector 64, and the guidewire 50 is then inserted through the proximal opening 32 until it is in the desired position. Then the guidewire 50 is removed out through the outside wall 30 of the guidewire lumen 20 as explained in more detail elsewhere. Removal of the guidewire 50 through the outside wall of the catheter shaft 12 permits conversion of the catheter from an over-the-wire catheter to a rapid exchange catheter that can be removed from the patient without extension of the guidewire 50.

In the embodiment illustrated in FIG. 6, because a conventional guidewire connector 64 is ordinarily used, back bleeding during use is eliminated by tightening the Tuehy- Borst adapter (not shown) except when manipulating the guidewire 50. This is in contrast to the embodiment illustrated in FIG. 1, where some back bleeding might be expected.

In yet another embodiment of the invention, the guidewire removal and reinsertion explained in connection with FIG. 6 is eliminated by providing a removable "Y" connector 80, illustrated in FIGS. 7-13.

Figure 7:
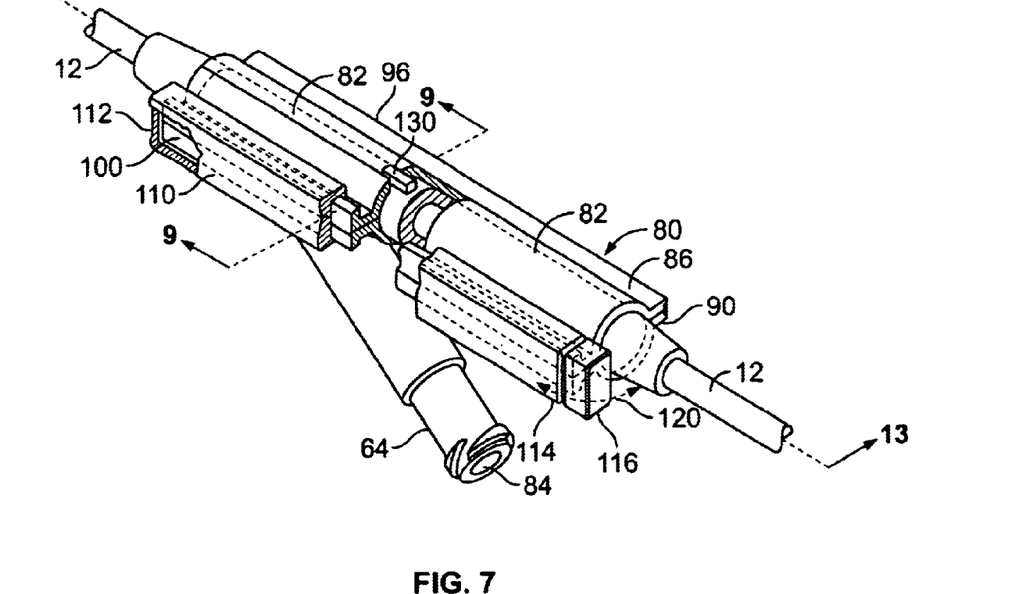
FIG. 7 is a perspective view of a removable "Y" connector at the proximal end of the catheter shaft.

The particular embodiment of removable "Y" connector illustrated in FIG. 7 provides an axially separable "Y" connector 80. The "Y" connector 80 is preferably molded of a relatively hard thermoplastic material, and is adapted to fit concentrically around the catheter shaft. The removable "Y" connector 80 is formed of 2 (or more) pieces which are joined together along lines extending in the axial or longitudinal direction of the catheter shaft 12. In the illustrated embodiment, the removable "Y" connector has an axial portion 82 through which the balloon lumen 22 (and preferably the catheter shaft 12) extends. The removable "Y" connector 80 further has a guidewire connector 64 extending proximally and at an angle outwardly from the axial portion 82 of the removable "Y" connector 80.

Figures 12, 13:
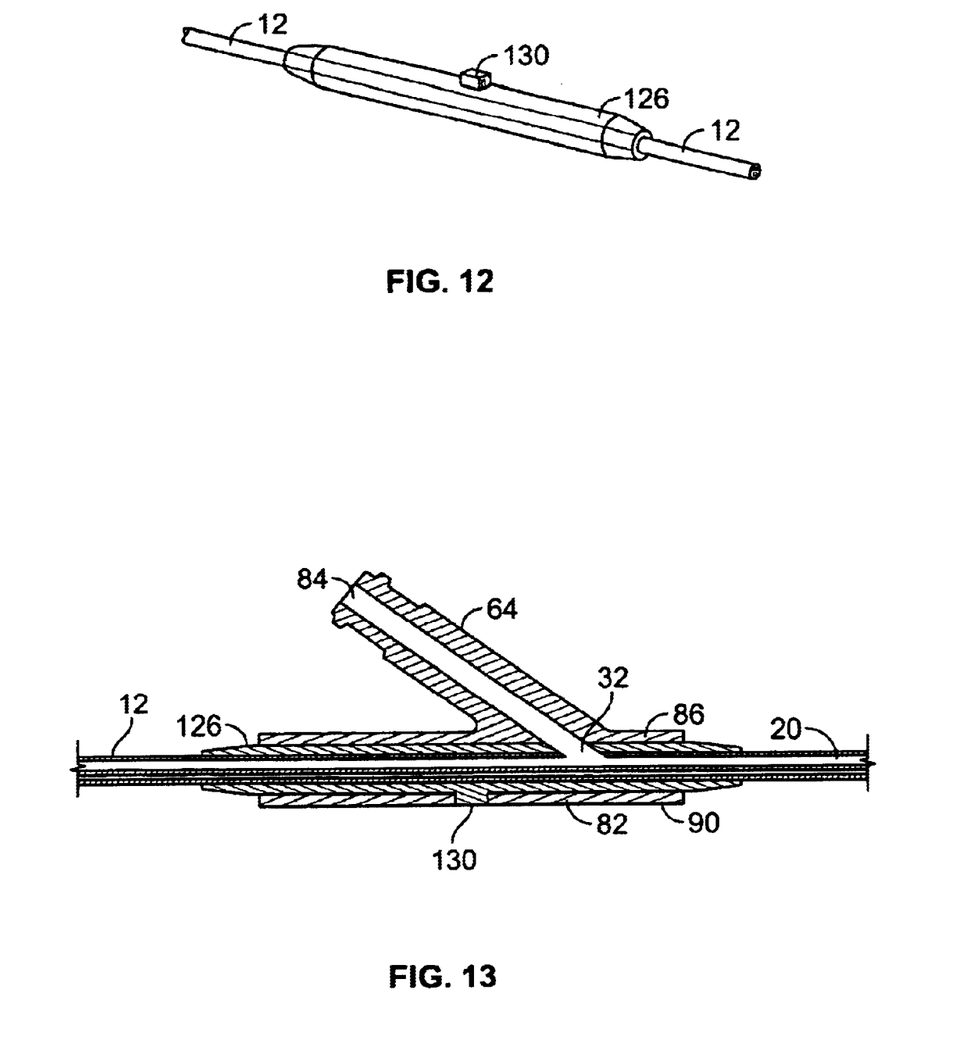
FIG. 12 is a perspective view of the distal end of the catheter shaft after removal of the "Y" connector, illustrating a sealing member.
FIG. 13 is a longitudinal cross section of the removable "Y" connector, taken along the line 13—13 in FIG. 7.

The guidewire connector 64 of the removable "Y" connector 80 is cylindrical in shape and has a guidewire bore 84 extending therethrough. The guidewire bore 84 connects through the proximal opening 32 into the guidewire lumen 20, as best illustrated in FIG. 13.

Figure 11:
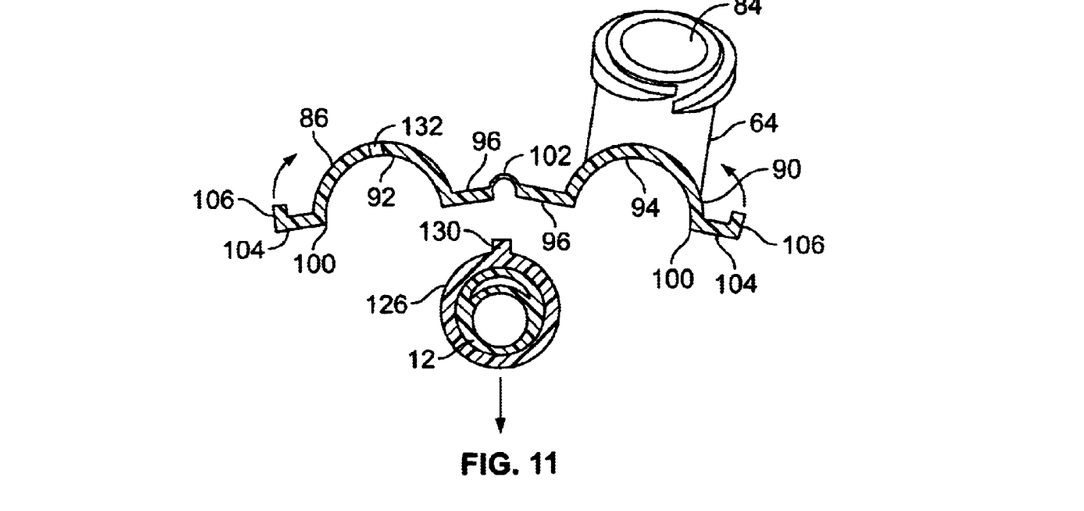
FIG. 11 is an exploded transverse cross section corresponding to FIG. 9, illustrating removal of the "Y" connector from the catheter shaft.

The removable "Y" connector 80 is preferably formed of a first half 86 and second half 90. The first half 86 and the second half 90 each has a semi cylindrical recess 92, 94 extending axially along the length of each half 86, 90 of the removable "Y" connector 80. The semi cylindrical recesses 92,94 are best illustrated in FIG. 11. When the first and second halves 86, 90 are joined together, the semi cylindrical recesses 92, 94 together form a cylindrical recess through which the catheter shaft 12 extends.

When the first and second halves 86, 90 are joined together on the catheter shaft 12, they are joined at a first edge 96 and a second edge 100 on opposite sides of the catheter shaft 12. The first and second edges 96, 100 of each half 86, 90 extend axially parallel to the axis of the catheter shaft 12.

In a preferred embodiment of the invention, the first edges 96 of the first and second halves 86, 90 are joined by a hinge 102. Preferably, the hinge 102 is a "live" hinge; that is, a hinge formed of a thin portion of the polymer material of which the removable "Y" connector 80 is formed. In a preferred embodiment, the hinge 102 extends axially the entire length of the first edge 96.

Figure 9:
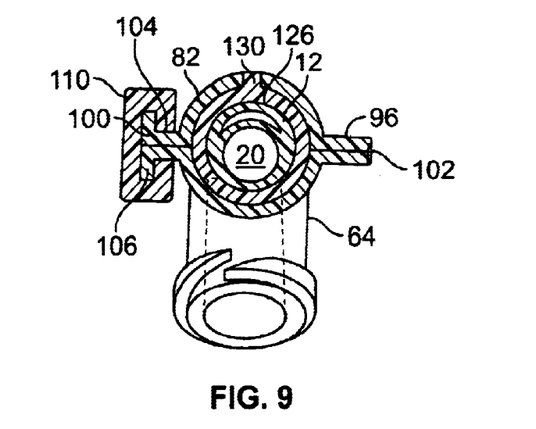
FIG. 9 is a transverse cross section taken along the line 9—9 in FIG. 7.

The second edges 100 of the first and second halves 86, 90 are separably joined together by any appropriate connecting mechanism. The illustrated mechanism is but one possibility. In the illustrated mechanism, the second edge 100 of the first and second halves 86, 90, comprises on each half a radially extending tab 104 running the length of the second edge 100. At the outside radial edge of the tabs 104 is a flange 106 formed so that, when the first and second halves 86, 90 are mated together at their second edges 100, the flanges 106 extend in opposite directions on the first and second halves 86, 90, forming a "T" shape in radial cross section as shown in FIG. 9.

Figure 8:
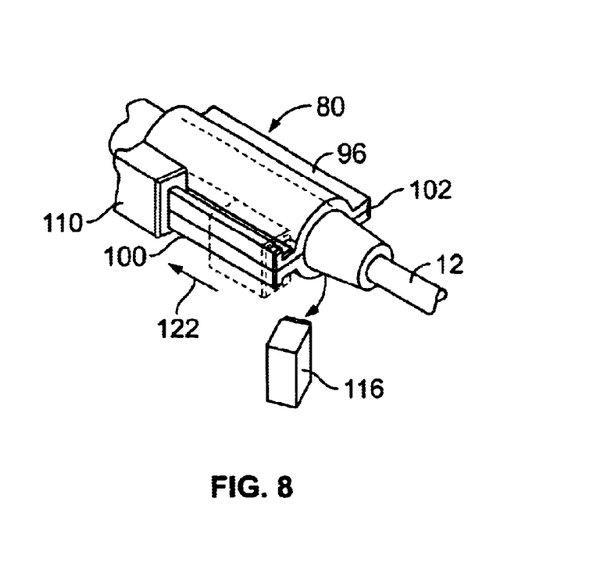
FIG. 8 is a detailed perspective view of a locking mechanism on the "Y" connector of FIG. 7.

An edge connector 110 is provided to hold the second edges 100 of the first and second halves 86, 90 together. The edge connector 110 preferably extends the entire length of the second edges 100 and is formed with a "T" channel inside to lock together the tabs 104 and flanges 106 of the second edges 100 of the first an second halves 86, 90. Thus, the "T" of the mated second edges of the first second edges 100 of the first and second halves 86, 90 is adapted to slide inside the "T" channel of the edge connector 110. Once the connector 110 is place on the "T" of the second edges, it may be locked in place using any appropriate mechanism. In one embodiment, a first end 112 of the connector is permanently closed to prevent movement of the edge connector 110 in one direction. The second end 114 of the edge connector 110 may have a breakaway end 116, as illustrated in FIGS. 7 and 8. The breakaway end 116 is glued or otherwise connected to the remainder of the connector 110 in such a manner that it may be readily severed from the edge connector 110. This may be done by a rocking motion applied to the breakaway end 116 as illustrated in by the arrows 120 in FIG. 7. Once the breakaway end 116 is removed as illustrated in FIG. 8, the connector 110 may be moved axially in the direction indicated by arrow 122 until the edge connector 110 is removed from the remainder of the removable "Y" connector 80.

Figure 10:
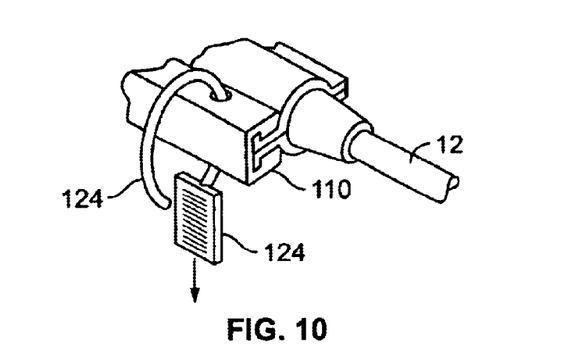
FIG. 10 is a detailed perspective view of another locking mechanism on the "Y" connector of FIG. 7.

Another method for locking the edge connector 110 onto the removable "Y" connector 80 is by use of a locking pin 124 as illustrated in FIG. 10. The locking pin may extend through the edge connector 110 and the second edges 100 of the first and second halves 86, 90, to lock the edge connector 100 in place. When the pin 124 is removed, the edge connector 110 may also be removed.

Although the pin 124 illustrated in FIG. 10 is circular, any other suitable pin or locking device may similarly be used.

After the removal of the edge connector 110, the first and second halves. 86, 90 may be removed from the catheter shaft 12 as illustrated in FIG. 11 by pivoting the second edges 100 away from each other. The removable "Y" connector 80 may then be slid proximally off the proximal end of the guidewire 50.

In a preferred embodiment of the invention, a seal 126 is provided around the catheter shaft 12 as illustrated in FIG. 12. The seal 126 prevents leakage between the removable "Y" connector 80 and the catheter shaft 12, and is preferably formed of annular polymer material such as elastomeric material or closed cell foam. The seal 126 is preferably provided with an index feature 130 for preventing rotational or longitudinal movement of the in-place "Y" connector 80 with respect to the catheter shaft 12. In the illustrated embodiment, the index feature 130 is an outwardly extending tab; however, the index feature 130 could alternatively be a groove, a recess, a flange, or the like. The outwardly-extending index feature 130 illustrated in FIGS. 12 and 11 can cooperate with a complimentary index receptacle 132 on the axial portion 82 of the removable "Y" connector 80.

Figure 14:
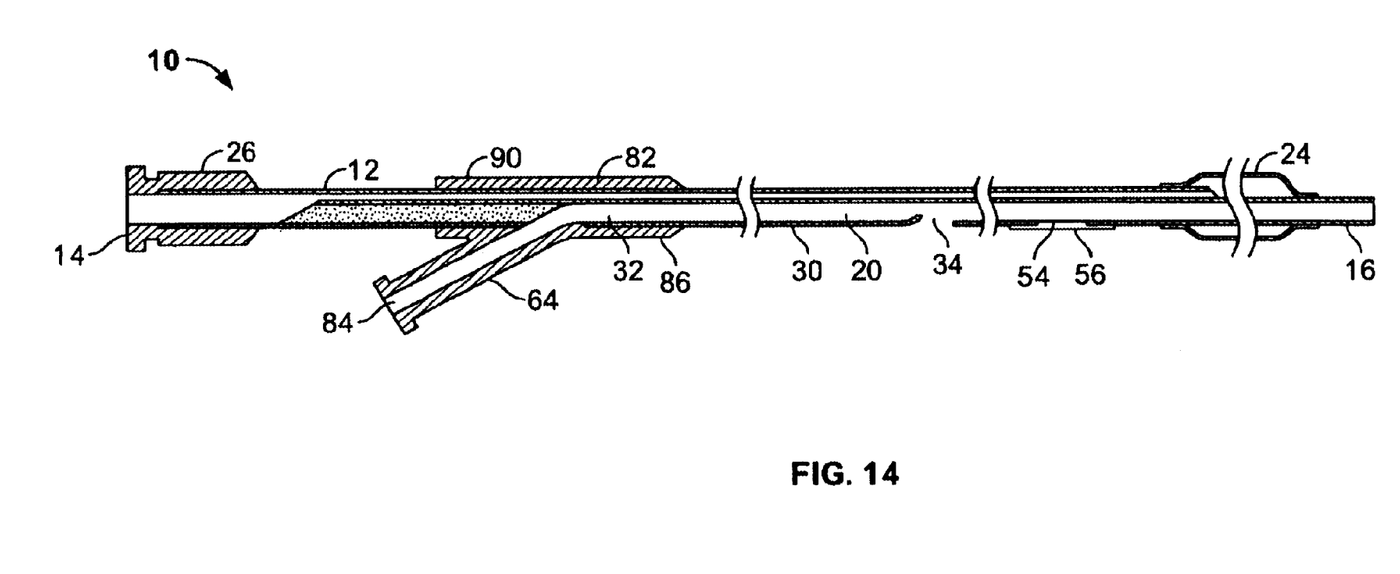
FIG. 14 is a longitudinal cross section of the entire catheter, taken along the line 13—13 in FIG. 7.
Figure 15:
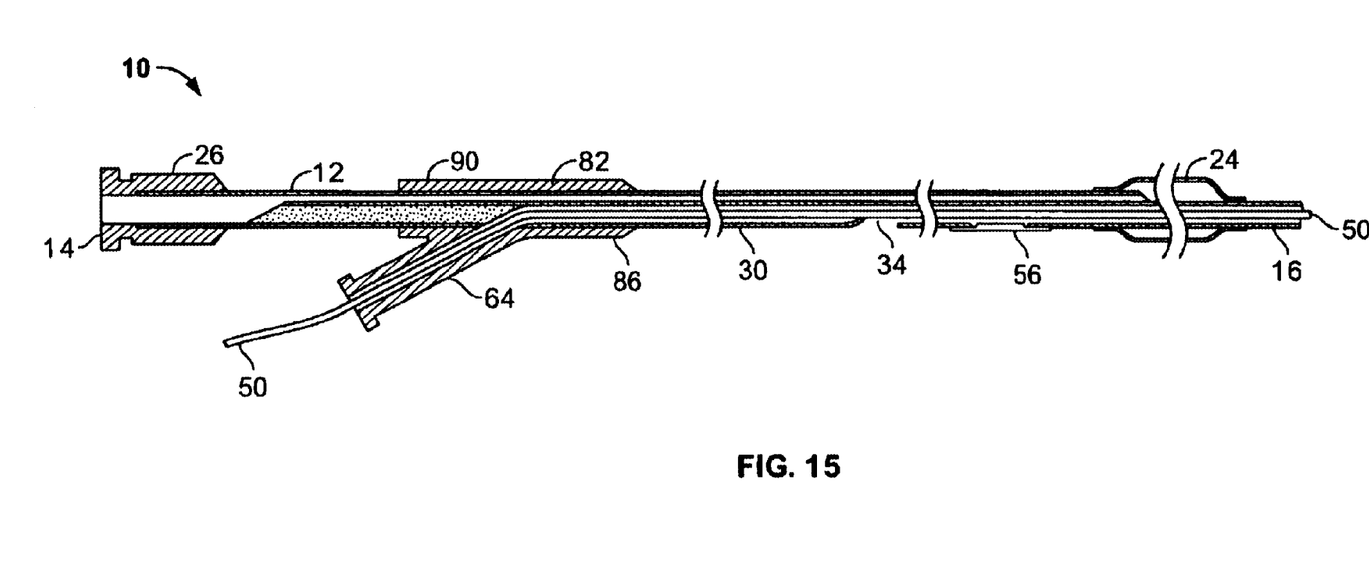
FIG. 15 corresponds to FIG. 14, except that the guidewire is illustrated in place in the guidewire lumen.

The use of the removable "Y" connector is further illustrated in FIGS. 14 and 15. The catheter 10 without the "Y" connector 80 in place is illustrated in FIG. 14. A guidewire 50 is inserted into the proximal opening 32 through the guidewire connector 64, as seen in FIG. 15. The guidewire 50 extends the length of the catheter shaft 12 and out of the distal end 16 of the catheter 10.

When the removable "Y" connector 80 is removed from the catheter shaft 12, the catheter 10 is properly illustrated in FIG. 3, and the guidewire 50 can be removed laterally through the outside wall 30 of the guidewire lumen 20 as illustrated in FIGS. 3 and 5, and as previously explained.

Although the removable "Y" connector 80 has been discussed in the context of a particular preferred embodiment, it will be understood that equivalent removable "Y" connectors can be provided in which only a portion (such as a strip) of the "Y" connector is removed from the catheter shaft 12; or where there are more than two separable pieces of the "Y" connector; where alternative latches or locking mechanisms are utilized to hold the removable "Y" connector together until removal is desired. Further, other mechanical features having equivalent function can be substituted for others of the various described elements.

Methods of Using the Convertible Mode Catheter

The catheter of the present invention may be used as a rapid exchange catheter with the guidewire 50 extending through the side port 34 and out of the distal end 16 of the guidewire lumen 20. Alternatively, it may be used as a conventional over the wire catheter with the guidewire 50 extending substantially the entire length of the catheter shaft 12 from the proximal end (either through a conventional "Y" connector 62 or a removable "Y" connector 80 or through the proximal opening 32) distally through the entire length of the catheter shaft and out of the distal end thereof.

A revolutionary aspect of the catheter of the present invention is that it may readily and rapidly be converted from one mode of use to the other. Thus, it can be used first as a rapid exchange catheter, with the guidewire extending in the guidewire lumen 20 only from the side port 34 to the distal end of the catheter. It can be converted from this rapid exchange mode of use to conventional over-the-wire use simply by removing the guidewire and, while maintaining the catheter 10 in place in the patient, inserting a new guidewire 50 into the proximal end of the guidewire lumen 20 (through a "Y" connector or through the proximal opening 32) and extending the guidewire 50 out of the distal end of the catheter 10.

When the catheter of FIG. 4 is being used as a conventional over the wire catheter, it can be converted into a rapid exchange catheter by removing the removable "Y" connector 80 (if used), and, with the guidewire extending proximally out of the proximal opening 32, maintaining the guidewire 50 in position in the patient while moving the guidewire laterally out of the outside wall 30 of the guidewire lumen 20 through the guidewire removing means 40 and simultaneously withdrawing the catheter 10 proximally until the distal end 16 of the catheter 10 is outside of the patient. During this portion of the procedure, the guidewire 50 is held by grasping it at the proximal end. Then the operator may hold the guidewire 50 by grasping the portion of the guidewire 50 exposed at the distal end 16 of the catheter 10, remove the catheter 10 off of the proximal end of the guidewire 50, and insert a new catheter 10 over the guidewire 50 while maintaining the position of the guidewire 50 in the patient. The insertion of the new catheter 10 may be accomplished in rapid exchange mode by retrograde insertion of the proximal end of the guidewire 50 through the distal end of the catheter and out of the side port 34. The proximal end of the guidewire is then held while the catheter 10 is advanced back into position in the patient. The catheter can then be used as a rapid exchange catheter. Alternatively, if desired, the guidewire 50 may be removed with the catheter maintained in position, and in a matter of seconds the guidewire may be reinserted through the proximal opening 32 or through the proximal end 14 of the catheter shaft 12 to convert the mode of use to conventional over the wire use.

Thus, it will be appreciated that the catheter of the present invention can easily be used in either a rapid exchange mode or an over the wire mode; that conversion between modes of use may be readily accomplished; that guidewire exchange may be accomplished in either mode of use, and that catheter exchange when in either mode of use can be accomplished without use of an extension guidewire; and that all of the forgoing conversions and modes of use can be accomplished while maintaining the positioning of either the guidewire or the catheter in the patient.

Thus, one method of the present invention comprises inserting the catheter of FIG. 1 into the patient with the guidewire 50 going through the proximal opening 32 and extending from that point distally through the entire remaining length of the catheter shaft 12 and out of the distal end 16. The guidewire 50 can then be exchanged by removing it and reinserting it through the proximal opening 32. The catheter can be exchanged by holding the guidewire as explained above while peeling away the catheter laterally while withdrawing it so that the guidewire is pulled through the guidewire removing means 40 until the distal end of the catheter is outside the patient. The guidewire is then held distally of the catheter and a new catheter is inserted, this time in rapid exchange mode. Once that catheter is in place, the guidewire can be rapidly exchanged (if desired) to convert the catheter back into the over-the-wire mode of use as explained above.

In another method of use, the catheter of FIG. 6 can be used. This catheter can be used with the guidewire in the side port or the proximal opening, as explained above, with the same catheter and guidewire exchanges possible. Moreover, it can be used with the guidewire extending through the entire length of the guidewire lumen 20 through the guidewire connector 64. Exchange of the guidewire from the guidewire connector 64 to the proximal opening 32 and vice versa is also contemplated.

The identical modes of use explained in connection with the FIG. 1 catheter can be used with the removable "Y" connector catheter of FIGS. 7-15, except the guidewire passes simultaneously through the proximal opening 32 and the guidewire adapter 64 of the removable "Y" connector 80. Further, in these modes of use, the conversion from over-the-wire use to rapid exchange use will require removal of the "Y" connector 80 prior to and in addition to use of the guidewire removing means 40.

Although the present invention has been described in the context of certain preferred embodiments, it is intended that the scope of the present patent be measured with reference with the appended claims and reasonable equivalence thereof.

What is claimed is:

1. An angioplasty catheter comprising:
    a catheter shaft having a proximal end, a distal end, and an angioplasty balloon mounted on said shaft near said distal end;
    a guidewire lumen extending through said shaft adapted for receiving a steerable guidewire, wherein said guidewire lumen has an outside wall and a permanently formed proximal opening at or near the proximal end of said shaft adapted for insertion of a guidewire into said guidewire lumen; and
    a slit in the outside wall of said guidewire lumen extending distally from said proximal opening at least about 40 cm. for permitting a guidewire, when deployed in said guidewire lumen to be moved laterally from the guidewire lumen through the outside wall of said guidewire lumen.

2. The catheter of claim 1, wherein the proximal opening is formed in the side of the catheter at a point distal of the proximal end of the catheter, further comprising a guidewire adapter in the proximal end of the catheter communicating with the guidewire lumen, so that a guidewire can be inserted into the guidewire lumen at the proximal portion of the catheter either through the guidewire adapter or through the proximal opening.

3. A method of removing a catheter during a procedure involving vascular catheterization, comprising the steps of:

providing a catheter according to claim 2 having a guidewire passing through said guidewire lumen from one of the proximal opening and the guidewire adapter to the distal opening thereof and positioning said catheter in a patient; and removing the guidewire while maintaining the positioning of the catheter and inserting said guidewire back into the guidewire lumen and out of the distal end of the catheter through the other of the proximal opening and the guidewire adapter.

4. A method of removing a catheter during a procedure involving vascular catheterization, comprising the steps of:

providing a catheter according to claim 1 having a guidewire passing through said guidewire lumen from the poximal opening to the distal opening thereof and positioning said catheter in a patient with the proximal end of the guidewire extending out of the proximal opening;

holding the proximal end of the guidewire to maintain the positioning of the guidewire in the patient while removing said catheter from said patient by moving the guidewire laterally out of the guidewire lumen through the slit until the entire catheter is outside the patient and a portion of the guidewire is exposed at the distal end of the catheter; and then holding said exposed portion of the guidewire and removing the catheter off of the proximal end of the guidewire.

* * * * *